(12) United States Patent
Johnson

(10) Patent No.: US 6,855,223 B2
(45) Date of Patent: Feb. 15, 2005

(54) METHOD OF MANUFACTURING AN ELASTICIZED COMPOSITE MATERIAL

(75) Inventor: Larry Kenneth Johnson, Milford, OH (US)

(73) Assignee: The Procter & Gamble Company, Cincinnati, OH (US)

(*) Notice: Subject to any disclaimer, the term of this patent is extended or adjusted under 35 U.S.C. 154(b) by 275 days.

(21) Appl. No.: 10/292,207

(22) Filed: Nov. 12, 2002

(65) Prior Publication Data

US 2003/0089454 A1 May 15, 2003

Related U.S. Application Data

(60) Provisional application No. 60/332,122, filed on Nov. 14, 2001.

(51) Int. Cl.[7] .................................................. A61F 13/15
(52) U.S. Cl. ....................... 156/177; 156/178; 156/179; 156/161; 156/200; 156/203; 156/259; 156/271
(58) Field of Search ............................... 156/161, 163, 156/164, 229, 169, 174, 177, 178, 179, 217, 221, 200, 201, 203, 204, 259, 271

(56) References Cited

U.S. PATENT DOCUMENTS

| | | | |
|---|---|---|---|
| 3,911,173 A | 10/1975 | Sprague, Jr. | |
| 4,116,892 A | 9/1978 | Schwarz | |
| 4,573,986 A | 3/1986 | Minetola et al. | |
| 4,648,928 A | * 3/1987 | Ales | 156/164 |
| 4,785,996 A | 11/1988 | Ziecker et al. | |
| 4,834,741 A | 5/1989 | Sabee | |
| 4,842,666 A | 6/1989 | Werenicz | |
| 5,143,679 A | 9/1992 | Weber et al. | |
| 5,156,793 A | 10/1992 | Buell et al. | |
| 5,167,897 A | 12/1992 | Weber et al. | |
| 5,422,172 A | 6/1995 | Wu | |
| 5,474,525 A | 12/1995 | Blott | |
| 5,518,801 A | 5/1996 | Chappell et al. | |
| 6,152,186 A | 11/2000 | Arney et al. | |

* cited by examiner

Primary Examiner—Jeff H. Aftergut
(74) Attorney, Agent, or Firm—Jack L. Oney, Jr.; Jay A. Krebs; Ken K. Patel

(57) ABSTRACT

A method of manufacturing an elasticized composite material including a multiplicity of elastic strips for use in garments, particularly in disposable absorbent articles is disclosed. The method includes the steps of folding the first substrate around the mandrel to form a tube while moving the tube longitudinally at a first velocity, and simultaneously winding at least one elastic strip around an outer surface of the tube at a second velocity to form a helical path. The elastic strip can be joined to the outer surface of the tube along the helical path to form a first composite tube. The method further includes the step of folding a second substrate around the first composite tube to cover the elastic strip and to form a second composite tube, which then can be slit longitudinally to form a planar composite material. Finally, the planar composite material can be activated to form the elasticized composite material.

23 Claims, 8 Drawing Sheets

METHOD OF MANUFACTURING AN ELASTICIZED COMPOSITE MATERIAL

This application claims the benefit of provisional application Ser. No. 60/332,122 filed Nov. 14,2001.

FIELD OF THE INVENTION

The present invention relates to a method of manufacturing a composite, flexible material having elasticized areas including a multiplicity of elastic strips. Its application is suited for use in garments, particularly in disposable absorbent articles.

BACKGROUND

Disposable absorbent articles, in particular, disposable diapers including pull-on diapers, often include elastic features designed to provide a more comfortable and contouring fit to a wearer (a baby or an adult suffering from incontinence) by conformably fitting the article to the wearer and sustaining this fit throughout the time of wear. Examples of such features include elastic side panels, elastic waist features, elastic leg cuffs and the like, providing expansion and contraction in certain directions to ensure a sustained fit. Often, such elastic features are required to be breathable to provide a desired comfort to the wearer.

The elastic features of disposable absorbent articles are often made of compound materials comprising elastic films (including breathable films) or elastic scrims, laminated with non-woven fabrics providing desired surface properties and aesthetics of the compound material. The elastic properties of such compound materials are often provided by activating the elastic properties which can be latent before the activation, that is the compound material which is non-elastic by itself before the activation becomes elastic after the activation as it were itself elastic.

One of the activation techniques can include mechanical stretching, preferably incremental mechanical stretching of the compound material to provide permanent elongation of the non-woven substrate(s) comprising the compound material to enable the elastic member(s) of the compound material, such as the elastic film or elastic scrim, to stretch under a tension force applied to the compound material. When the elastic member is allowed to contract, the permanently elongated nonwoven fabric wrinkles or shirrs to contract in dimension along with the elastic member. Such a compound material becomes elastic or elasticized material.

The elasticized materials are often expensive because they can not only include expensive elastic materials but also require difficult process operations of handling elastic films and scrims, for example, sophisticated cut and slip operations. Because the elasticized features are relatively expensive, they normally contribute to a higher cost of the disposable absorbent articles including such features.

Further, the elastic features of disposable absorbent articles are often required to have different elastic properties in different directions corresponding with the directions of different tension forces to which an absorbent disposable article can be subjected during wear. For example, elastic side panels can require different tension forces directed to the waist area rather than to the leg area of the article. This can be difficult to provide by use of elastic films or elastic scrims, which normally extend throughout the entire area of the side panels and, therefore, can be not sufficient to provide the desired different directional stretch properties. Alternatively, use of multiple, discrete pieces of elastic films or scrims positioned along the desired directions of the tension forces can be expensive due to the difficulties in handling the discrete pieces of elastic films or elastic scrims.

Therefore, it would be beneficial to provide a relatively low cost disposable absorbent article having desired elastic features. Further, it would be beneficial to provide a relatively low cost disposable absorbent article including desired elastic features having desired stretch properties in desired directions. It would be also beneficial to provide a relatively low cost elastic material suitable for use in designing such elastic features. Further, it would be beneficial to provide a latent elastic material suitable for use in disposable absorbent articles, which can be activated when desired, for example, during the production of the article to provide a desired elastic feature. Furthermore, it would be beneficial to provide a relatively low cost method of manufacturing such elastic and latent elastic materials.

SUMMARY OF THE INVENTION

In response to the difficulties and problems discussed above, a new method for manufacturing a lower-cost material suitable for use in elasticized features of disposable absorbent articles has been discovered.

In one aspect, the present invention concerns a method of manufacturing an elasticized composite material including one or more elastic strips. The method includes the steps of providing a mandrel, providing a first substrate and folding the first substrate around the mandrel to form a tube. The method further includes the steps of providing at least one elastic strip and moving the tube longitudinally at a first velocity and simultaneously winding the at least one elastic strip around an outer surface of the tube at a second velocity to form a helical path. The method further includes the steps of joining the at least one elastic strip to the outer surface of the tube at least partially along the helical path to form a first composite tube and folding a second substrate around the first composite tube to cover the at least one elastic strip to form a second composite tube. The method further includes the steps of slitting the second composite tube longitudinally to open the second composite tube and unfolding the slit second composite tube to form a planar composite material. Finally, the method includes the step of activating the planar composite material to form the elasticized composite material.

In another aspect, the method includes the steps of providing a mandrel, providing a first substrate and folding the first substrate around the mandrel to form a tube. The method further includes the steps of providing at least one elastic strip and moving the tube longitudinally at a first velocity and simultaneously winding the at least one elastic strip around an outer surface of the tube at a second velocity to form a helical path. The method further includes the steps of joining the at least one elastic strip to the outer surface of the tube at least partially along the helical path to form a first composite tube and slitting the composite tube longitudinally to open the composite tube. The method further includes the steps of unfolding the slit composite tube to form a first planar composite material and folding the first planar composite material longitudinally forming a second planar composite material having the elastics strips disposed inside of the second planar composite material forming a crisscross pattern. Finally, the method includes the step of activating the second planar composite material to form the elasticized composite material.

The mandrel can have a cross-section shape selected from the group consisting of a circle, an oval, a triangle, a square, a trapezoid, a parallelogram, a polygon, and any combination thereof. The first substrate can be selected from a group consisting of a woven fabric, a knit fabric, a nonwoven fabric, a polymeric film, an elastic film, an elastic breathable film or any combination thereof. The first velocity or the second velocity can vary. The elastic strip can be selected from a group consisting of a natural rubber, a synthetic rubber, polyurethane elastomers, polyisoprene elastomers, styrene-isoprene-styrene elastomers, block copolymer elastomers and any combination thereof. The elastic strip can have a cross-sectional shape selected from a group consisting of a rectangle, a trapezoid, a round, an oval and any combination thereof.

BRIEF DESCRIPTION OF THE DRAWINGS

While the specification concludes with claims particularly pointing out and distinctly claiming the subject matter, which is regarded as the present invention, it is believed that the invention will be more fully understood from the following description taken in conjunction with the accompanying drawings, in which:

DETAILED DESCRIPTION OF THE INVENTION

The method of the present invention is suited for manufacturing a composite, flexible material having elasticized areas including a multiplicity of elastic strips. Its application is suited for use in garments, particularly in disposable absorbent articles.

As used herein, the term "absorbent article" refers to a device which absorbs and contains body exudates, and more specifically, refers to a device which is placed against the skin of a wearer to absorb and contain the various exudates discharged from the body. Examples of absorbent articles include diapers, pull-on pants, training pants, incontinence briefs, diaper holders, feminine hygiene garments, and the like.

The terms "pull-on diaper" and/or "training pants" refer herein to disposable absorbent articles typically having a fixed, closed configuration around the waist of the wearer and, which are intended to be put on the wearer by pulling the article over the legs of the wearer.

The term "disposable" is used herein to describe absorbent articles, which generally are not intended to be laundered or otherwise restored or reused as absorbent articles (i.e., they are intended to be discarded after a single use and, preferably, to be recycled, composted or otherwise discarded in an environmentally compatible manner).

The term "elastic" refers herein to any material that upon application of a force to its relaxed, initial length can stretch or elongate to its elongated length without rupture and breakage, and which can substantially recover its initial length upon release of the applied force.

The term "elasticized" refers herein to any elastic material comprising one or more elastic members and one or more nonwoven fabrics, which were activated to provide permanent elongation of the non-woven fabrics to enable the elastic members to stretch under application of a tension force.

The term "latent elastic material" refers herein to a compound material which by itself can be substantially non-elastic or partially elastic before activating its latent elastic properties.

The term "compound material" refers herein to at least two materials secured to one another, either intermittently or substantially continuously, along at least a portion of their coextensive surfaces.

The term "breathable" refers herein to any material suitable for use in garments or disposable absorbent articles, which is capable of transmitting air vapor to provide desired comfort to the wearer.

Figure 1:
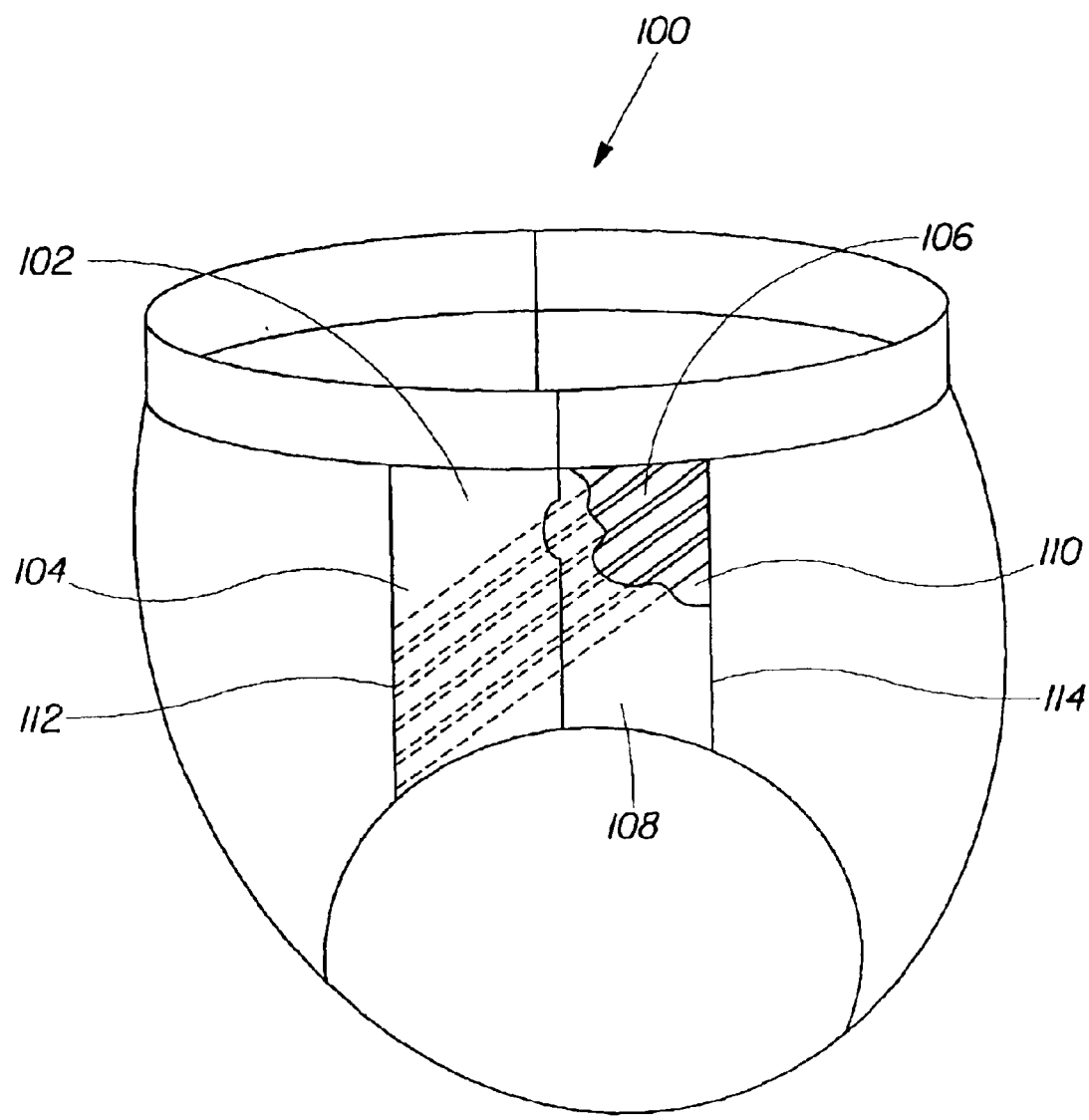
FIG. 1 is a simplified isometric view representatively illustrating one exemplary embodiment of a disposable absorbent article of the present invention having elastic side panels comprised of one embodiment of a material manufactured by the method of the present invention.

Referring now to the drawings, and more particularly to FIG. 1, there is shown one exemplary embodiment of a disposable absorbent article 100 of the present invention having breathable, elasticized side panels 102 comprising a composite material 104, which can be manufactured by the method of the present invention. The composite material 104 includes elastic strips 106 laminated between opposing an outer substrate 108 and an inner substrate 110 extending between longitudinal edges 112 and 114 of the side panel 102.

Figure 2:
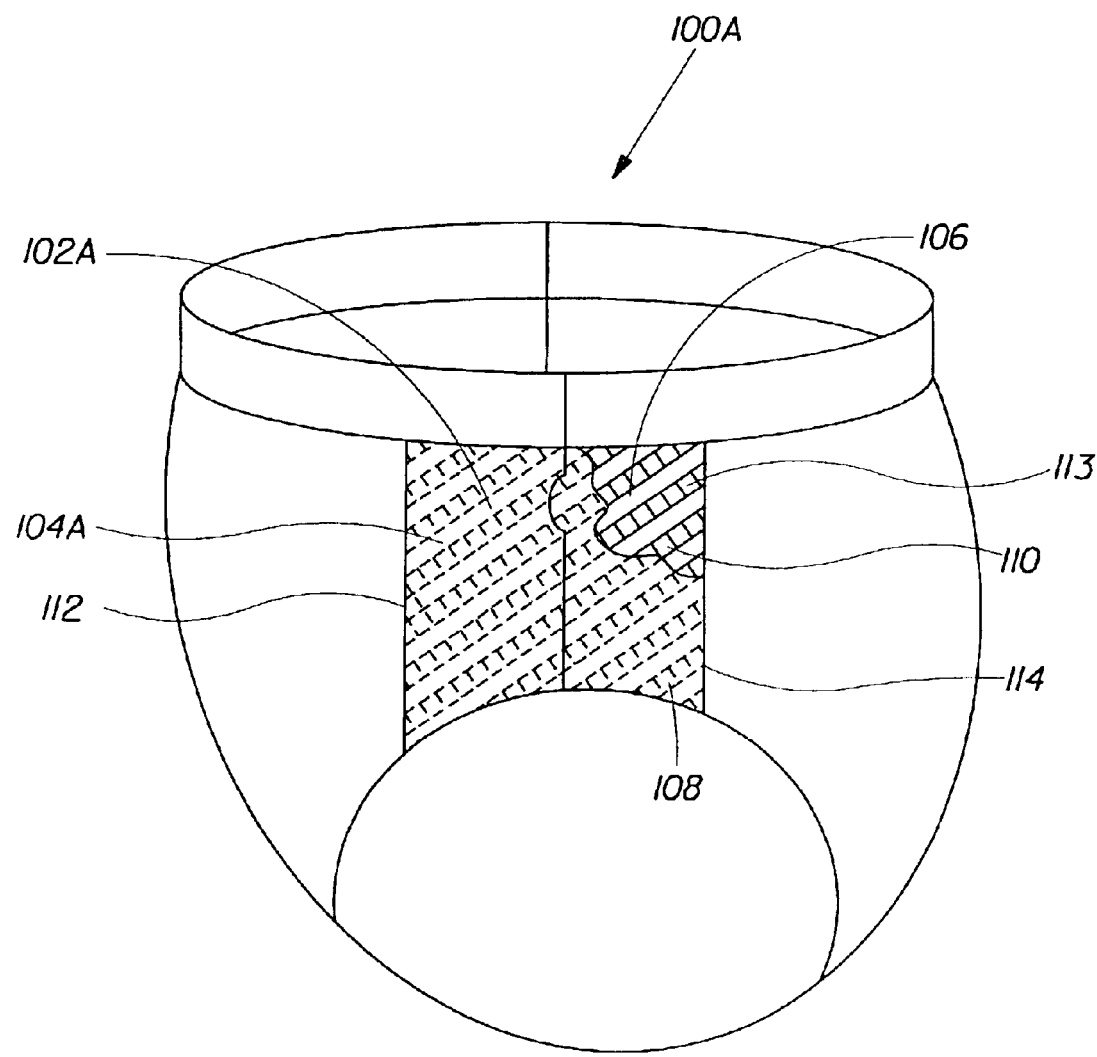
FIG. 2 is a simplified isometric view representatively illustrating another exemplary embodiment of a disposable absorbent article of the present invention having elastic side panels comprised of another embodiment of a material manufactured by the method of the present invention.

FIG. 2 illustrates another exemplary embodiment of a disposable absorbent article 110A of the present invention having breathable, elasticized side panels 102A comprising a composite material 104A, which can be manufactured by the method of the present invention. The composite material 104A includes elastic strips 106 laminated between opposing an outer substrate 108 and an inner substrate 110 extending between longitudinal edges 112 and 114 of the side panel 102A, forming a crisscross configuration 113.

Referring to FIGS. 1 and 2, the number of the elastic strips 106 can be any suitable number capable of providing a desired product performance. The elastic strips 106 can have any desired cross-sectional shape, such as rectangle, trapezoid, round, oval, irregular or the like, as well as any combination thereof. The larger dimension in the cross-section of the elastic strips 106 can be any suitable dimension ranging from about 1 mm to 35 mm and greater; preferably from about 6 mm to about 35 mm.

The elastic strips 106 can be composed of any desired elastic material, such as natural rubber, synthetic rubber, polyurethane elastomers, polyisoprene elastomers, styrene-isoprene-styrene elastomers, block copolymer elastomers or the like, as well as any combination thereof. In a preferred embodiment of the present invention, the elastic strips 106 are LYCRA elastomers available from E. I. DuPont de Nemours and Company having offices in Wilmington, Del.

Referring to FIGS. 1 and 2, the outer substrate 108 and the inner substrate 110, comprising the side panels 102 and 102A, can be any substrate suitable for use in garments and/or disposable absorbent articles, preferably breathable and skin-friendly material, composed of natural or synthetic components. Examples of such materials can include a woven fabric, a knit fabric, a nonwoven fabric, a polymeric film, an elastic film, an elastic breathable film or any combination thereof. In addition, the outer substrate 108 and the inner substrate 110 can be a single-layer or a multi-layer material comprising non-woven materials or combinations of nonwoven materials and elastic films, wherein the layers can be affixed or not affixed to each other.

The elastic strips 106 can be joined to the outer substrate 108 and/or inner substrate 110 by any suitable attachment means. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

In addition, the elastic strips 106 can be joined to the outer substrate 108 and/or the inner substrate 110 intermittently or substantially continuously. The term "intermittently" refers herein to elastic strips 106 which are joined to a substrate at discrete, spaced apart areas. Conversely, the term "substantially continuously" refers herein to elastic strips 106 which are joined to a substrate substantially continuously throughout the interface area.

Referring to FIGS. 1 and 2, the composite materials 104 and 104A of the present invention, composing the side panel 102 and 102A, respectively, can comprise identical or different elastic strips 106, wherein different elastic strips can be adjacent to each other, forming any suitable groupings or combinations of identical or different strips. In addition, the adjacent elastics strips 106 can be spaced from each other or contacting each other. The spacing between adjacent elastic strips 106 can vary from zero mm to about 10 mm, preferably from about 3 mm to about 5 mm.

Figure 3:
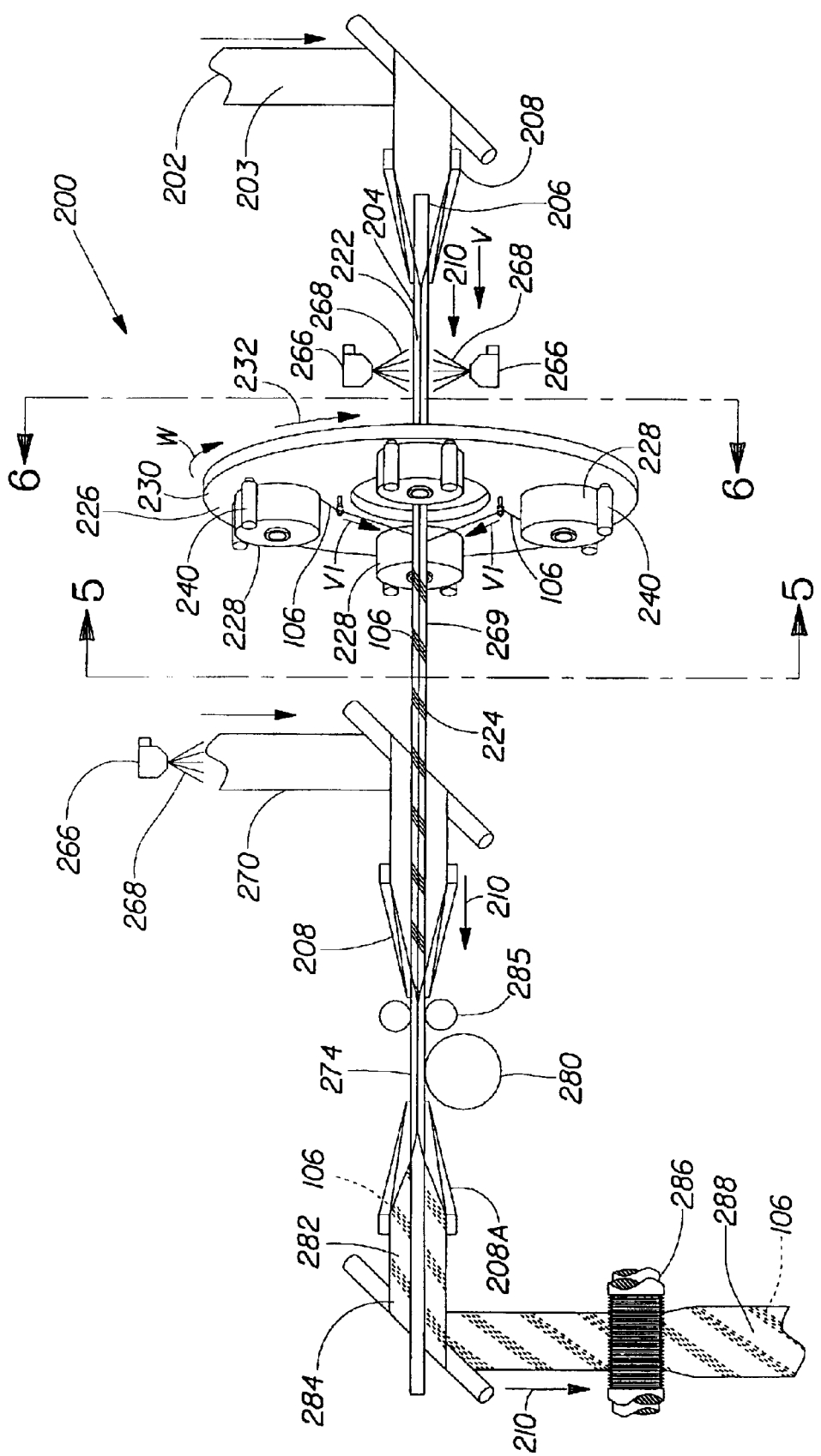
FIG. 3 is a simplified isometric view of one embodiment of the method and apparatus of the present invention.
Figure 4:
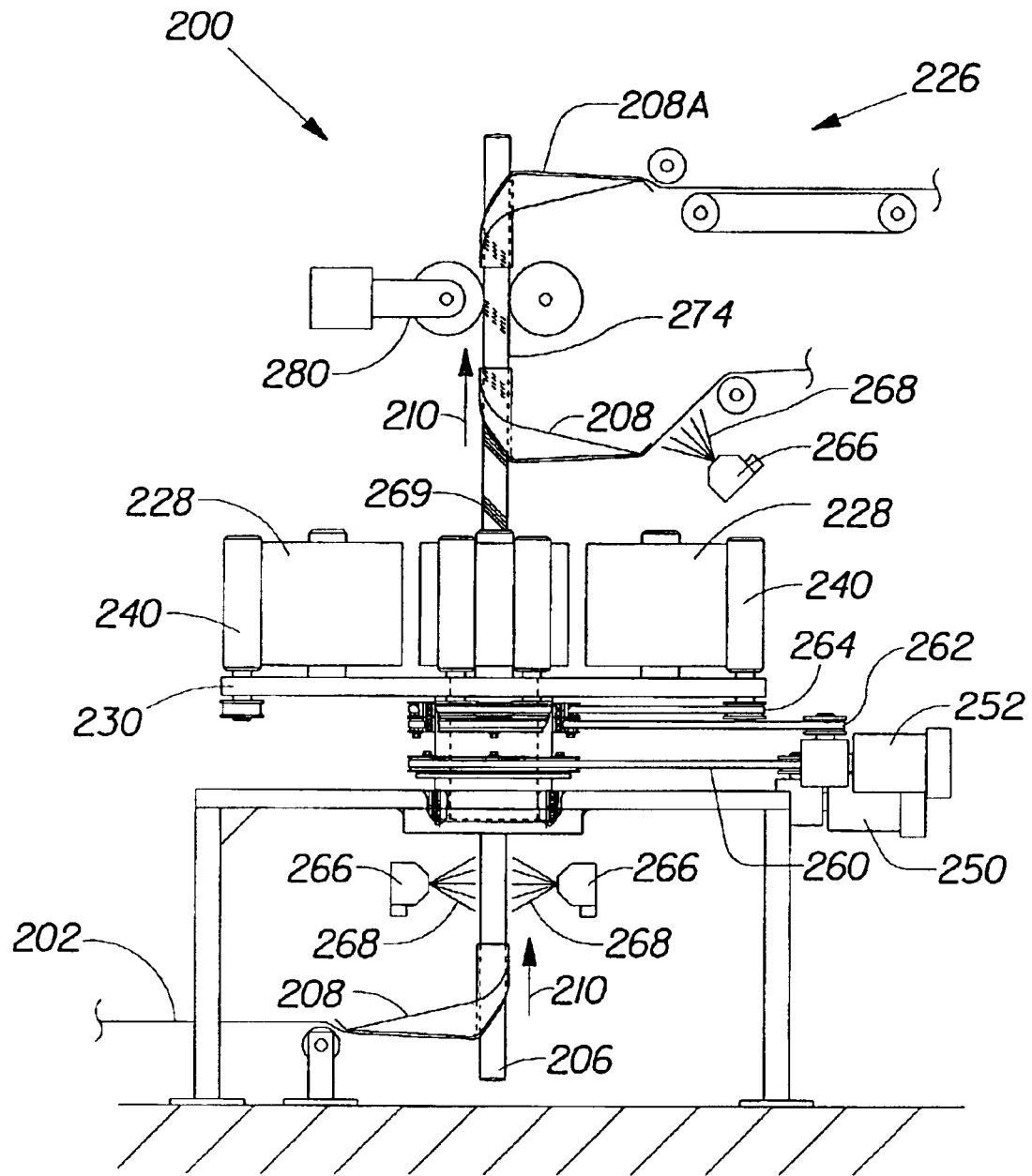
FIG. 4 is a simplified front elevation view of a winding device shown in FIG. 3.
Figure 5:
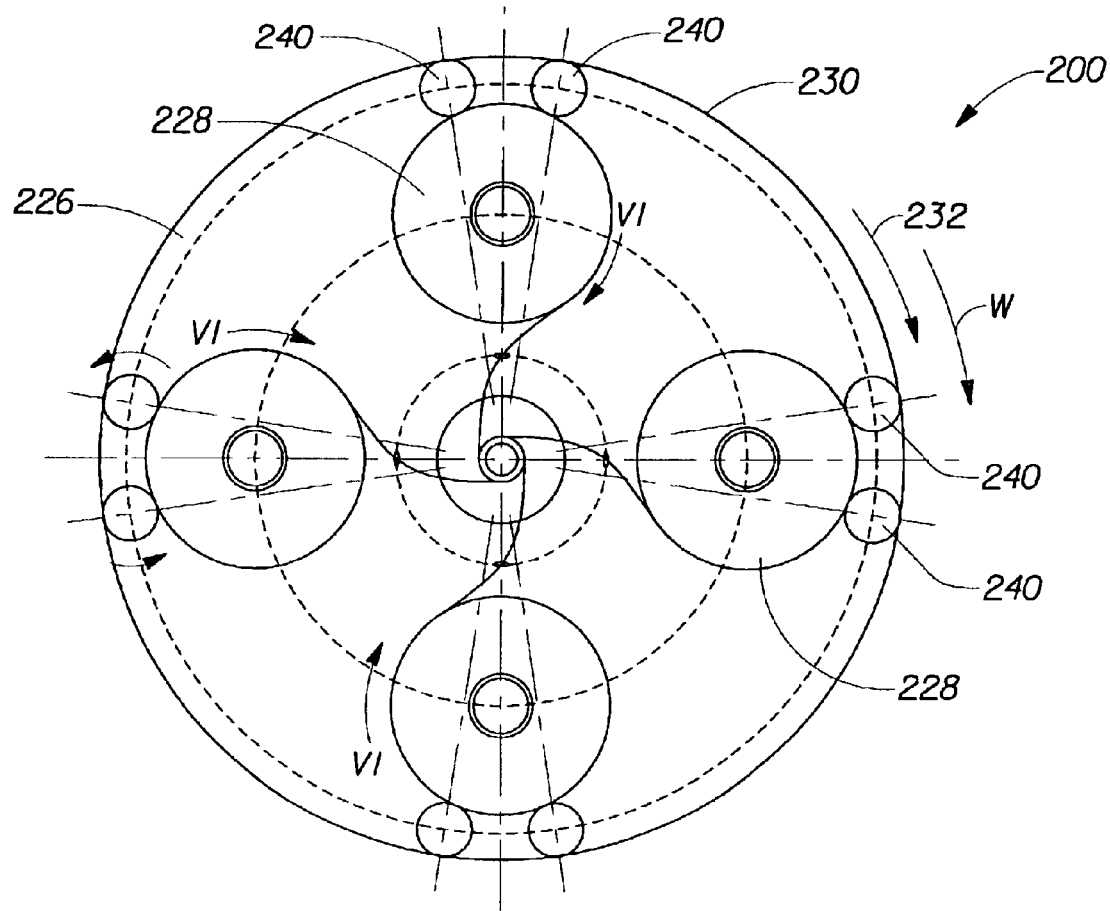
FIG. 5 is simplified cross-sectional view at a spool side of a winding device shown in FIG. 3, taken along lines 5—5.
Figure 6:
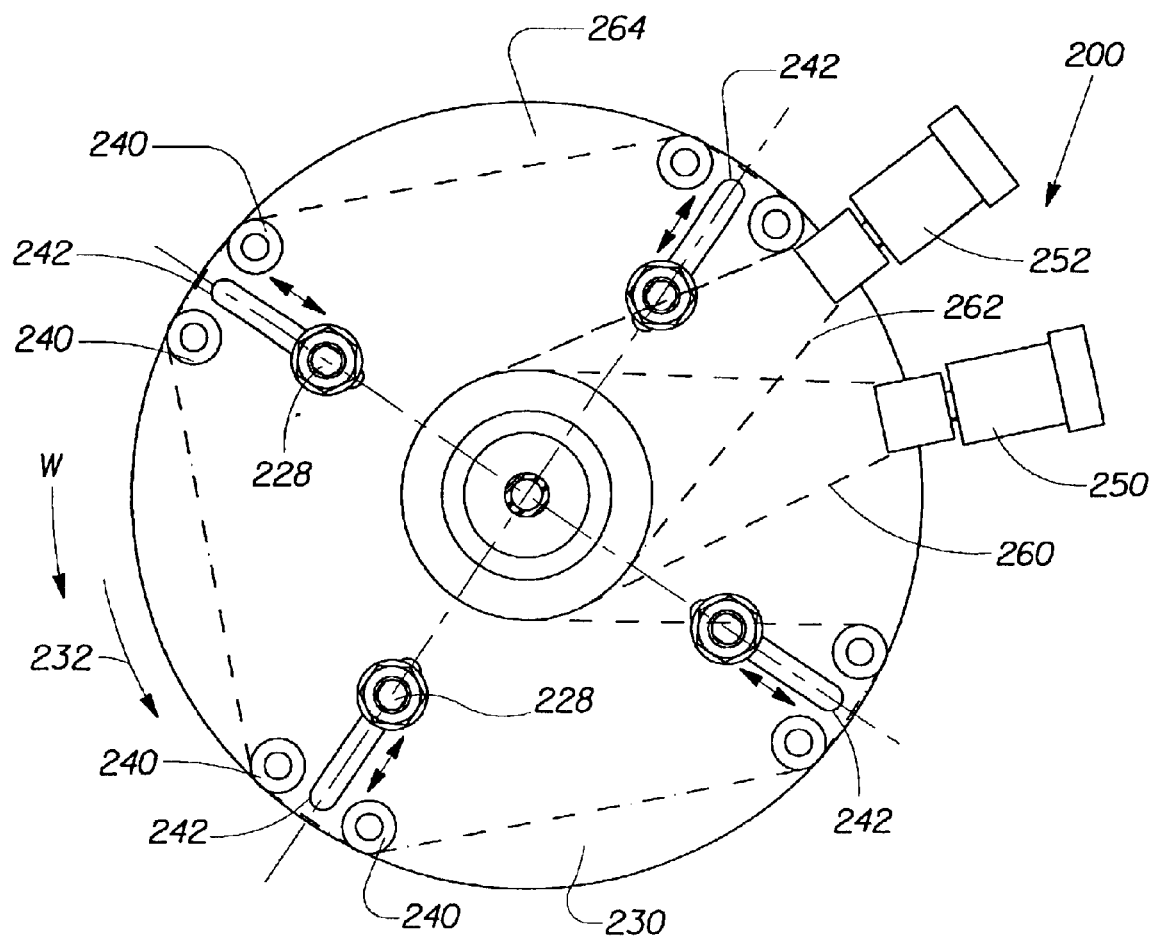
FIG. 6 is a simplified cross-sectional view at a drive side of a winding device shown in FIG. 3, taken along lines 6—6.

FIGS. 3–6 illustrate one embodiment of the method and apparatus 200 of the present invention for producing a material of the present invention, which includes one or more elastic strips joined to one or more substrates. FIG. 3 is a simplified isometric view of the embodiment 200; FIG. 4 is a front elevation view of a winding device shown in FIG. 3; FIG. 5 is a side cross-sectional view of the spool side of the winding device of FIG. 3, taken along lines 5–5; and FIG. 6 is a side cross-sectional view of the drive side of the winding device of FIG. 3, taken along lines 5–5.

Referring to FIG. 3, a first substrate 202 can be provided substantially continuously from any suitable supply means, such as a supply roll or box, having one beginning and one ending point on the supply means. The first substrate 202 can be provided by moving in a longitudinal direction 210 at a velocity V, which can range from about 10 meters per minute to about 1,000 meters per minute, preferably from about 30 meters per minute to about 500 meters per minute. (It should be noted that the longitudinal direction 210 can extend in any direction along the desirable path of travel of the first substrate 202.)

As described above, the first substrate 202 can be any substrate suitable for use in garments and/or disposable absorbent articles, preferably breathable and skin-friendly material, composed of natural or synthetic components. Examples of such materials can include a woven fabric, a knit fabric, a nonwoven fabric, a polymeric film, an elastic film, an elastic breathable film or any combination thereof. In addition, the first substrate 202 can be a single-layer or a multi-layer material comprising non-woven materials or combinations of non-woven materials and elastic films, wherein the layers can be joined or not joined to each other.

The first substrate 202 can be provided in a form of a continuous web 203, which can then be folded into a continuous tube 204 around a mandrel 206 by any suitable folding device 208 known to one skilled in the art. The mandrel 206 extending longitudinally inside of the folding device 208, can have any desired cross-sectional shape, such as a circle, an oval, a triangle, a square, a trapezoid, a parallelogram, a polygon, irregular shape or the like, as well as any combination thereof. The larger dimension in the cross-section of the mandrel 206 can be any suitable dimension ranging from about 10 mm to greater than 300 mm; preferably from about 20 mm to about 200 mm.

Alternatively, the first substrate 202 can be provided in a form of a continuous tube 204 fed onto the mandrel 206 extending longitudinally inside of the tube 204. Such an option will eliminate the need for the folding device 208. The tube 204 can be provided substantially continuously from any suitable supply means, such as a supply roll or box, having one beginning and one ending point on the supply means. The tube 204 can have any suitable width ranging from about 10 mm to greater than 300 mm, preferably from about 20 mm to about 200 mm.

The tube 204 moving longitudinally in the direction 210 can then be combined with at least one continuous elastic strip 106 wounded around an outer surface 222 of the tube 204. (It should be noted that during the winding of the strips 106 around the outer surface 222 of the tube 204, the tube 204 is preferably to move in the direction 212 vertically so as to minimize the possible negative effect of gravitational forces during the strip winding operation.) The number of elastic strips 106, each forming its own helical path 224, can be any suitable number. In one exemplary embodiment 200 shown in FIGS. 3–6, there are four elastic threads 106 forming four helical paths 224 extending longitudinally on the outer surface 222 of the tube 204, as shown in FIG. 3.

As was described before, the elastic strips 106 can have any desired cross-sectional shape, such as rectangle, trapezoid, round, oval, irregular or the like, as well as any combination thereof. The larger dimension in the cross-section of the elastic strip 106 can be any suitable dimension ranging from about 1 mm to 35 mm and greater; preferably from about 6 mm to about 35 mm. The elastic strip 106 can be composed of any desired elastic material, such as natural rubber, synthetic rubber, polyurethane elastomers, polyisoprene elastomers, styrene-isoprene-styrene elastomers, block copolymer elastomers or the like, as well as any combination thereof. In a preferred embodiment of the present invention, the elastic strip 106 is LYCRA elastomer available from E.I. DuPont de Nemours and Company having offices in Wilmington, Del.

The elastic strip 106 can be wound around the tube 204 by any means suitable to wind one or more elastic threads 106 around the tube 204. An example of a winding device 226 is illustrated in FIGS. 3–6, having four spools 228 (however, the number of spools 228 can be any suitable number) mounted to a spool holder 230 situated co-axially with the mandrel 206 extending inside of the spool holder 230 in the direction 210, which can preferably be directed vertically to minimize the possible negative effects of gravitational forces on the winding operation. The spool holder 230 is disposed preferably perpendicular to the longitudinal direction 210 and rotates around the mandrel 206 in a direction 232 at an angular velocity W. The spool holder 230 can rotate in a direction opposite to the direction 232, if desired. The angular velocity W can vary, if desired.

The elastic threads 106 can be supplied and metered from their respective spools 228 by any suitable means, for example, by an unwind mechanism 240, which can be driven at a desired speed to provide a desired metering speed V1 (see FIG. 3) of the elastic strips 106. The spools 228 can be held and maintained against the unwind mechanisms 240 by any suitable means, including a spring-loaded force, under which the spools 228 can move in relation to the unwinding mechanisms 240 radially, along radial slots 242 in the spoon holder 230. (It should be noted that, alternatively, the unwinding mechanisms 240 can move in relation to the spools 228 to maintain the desired engagement between the spools 228 and the unwinding mechanisms 240.) The metering speed V1 of the elastic strips 106 can vary to provide a desired tension or stretch of the elastics strips 106 for winding the elastic strips 106 around the tube 204 at a desired tension or stretch. The elastic strips 106 can be wound around the tube 204 at any desired stretch ranging from about zero % to about 500%, preferably from zero % to about 300.

The spool holder 230 and the unwind mechanisms 240 can be driven by any suitable means known to one skilled in the art. One example of a suitable drive arrangement is illustrated in a simplistic manner in FIGS. 5 and 6, wherein a motor 250 can drive the spoon holder 230 via a belt 260. Another motor 252 can drive the spoon unwinds 240 via a belt 262 communicating with a belt 264 that can directly drive the spoon unwinds 240. The motors 250 and 252 can be any suitable motors known to one skilled in the art, including DC motors, AC motors, servo motors and the like, having desired speed or torque capabilities.

The elastic strips 106 can be joined to the tube 204 by any suitable joining means described herein above. FIG. 3 illustrates an example of joining the elastic strips 106 to the tube 204 by an adhesive device 266 applying a suitable adhesive 268 (described herein above) onto the outer surface 222 of the tube 204 before combining the elastic strips 106 with the tube 204. Alternatively, it should be noted that the adhesive 268 can be applied onto the elastic strips 106 before and after the combining of the elastics strips 106 with the outer surface 222.

Referring to FIG. 3, after the elastics strips 106 are wound around the tube 204 to form a first composite tube 269, a second substrate 270 can be folded around the first composite tube 269 by any suitable folding device 208 to form a second composite tube 274. The second substrate 270 can be joined to the first composite tube 269 by any suitable joining means described herein above. FIG. 3 illustrates an example of joining the second substrate 270 by an adhesive device 266 applying a suitable adhesive 268 (described herein above) onto the second substrate 270.

After the second composite tube 274 is formed, it can be slit longitudinally by any suitable slitting device 280 (for clarity of illustration, shown in FIG. 3 in an out of plane position) so as to then to open the slit second composite tube 274 longitudinally by any suitable unfolding device 208A to form a planar composite material 282. The planar composite material 282 can be a latent elastic material 284 comprising elastic strips 106 in a substantially relaxed or stretched condition bonded between two opposing substrates 202 and 270. If the substrates 202 and 270 are not elastic, then the latent elastic material 284 is not elastic. The term "latent elastic material" refers herein to a compound material which by itself can be substantially non-elastic or partially elastic before elasticizing its latent elastic properties.

The latent elastic material 284 can be elasticized by activation. The term "elasticizing" or "elasticized" refers herein to any elastic material comprising one or more elastic members and one or more substrates, which are activated to provide incremental permanent elongation of the substrates to enable the elastic members to stretch under application of a tension force. The term "activation" refers herein to a process sometimes referred to as a "ring-rolling" process utilizing corrugated inter-engaging rolls to permanently elongate the substrate to reduce its resistance to stretch. The resulted "elasticized" composite material has greater degree of stretchability in the regions that have been subjected to the ring-rolling process. The methods for imparting stretchability to an otherwise substantially inelastic material by using corrugated rolls, which laterally or longitudinally stretch and permanently deform the material, are disclosed in U.S. Pat. No. 4,116,892, issued on Sep. 26, 1978, to E. C. A. Schwarz; U.S. Pat. No. 4,834,741, issued on May 30, 1989, to R. N. Sabee; U.S. Pat. No. 5,143,679, issued on Sep. 1, 1992, to G. M. Weber et al., U.S. Pat. No. 5,156,793, issued on Oct. 20, 1992, to K B. Bell et al.; U.S. Pat. No. 5,167,897, issued on Dec. 1, 1992, to G. M. Weber et al; U.S. Pat. No. 5,422,172, issued on Jun. 6, 1995, to P.-C. Wu; and U.S. Pat. No. 5,518,801, issued on May 21, 1996 to C. W. Chappell et al. Each of these patents is hereby incorporated by reference.

Referring to FIG. 3, the latent elastic material 284 can then be elasticized or activated by an activation device 286, which incrementally stretches the latent elastic material 284 to provide permanent elongation of the first and second substrates 202 and 270, respectively. The resultant elasticized compound material 288 becomes an elastic material, wherein the elastic strips 106 can stretch under a tension force applied to the elasticized compound material 288. Depending on the stretching properties of the elastic strips 106, the elasticized composite material 288 can be stretched under a tension force within the provided permanent elongation of the substrates 202 and 270.

Figure 7:
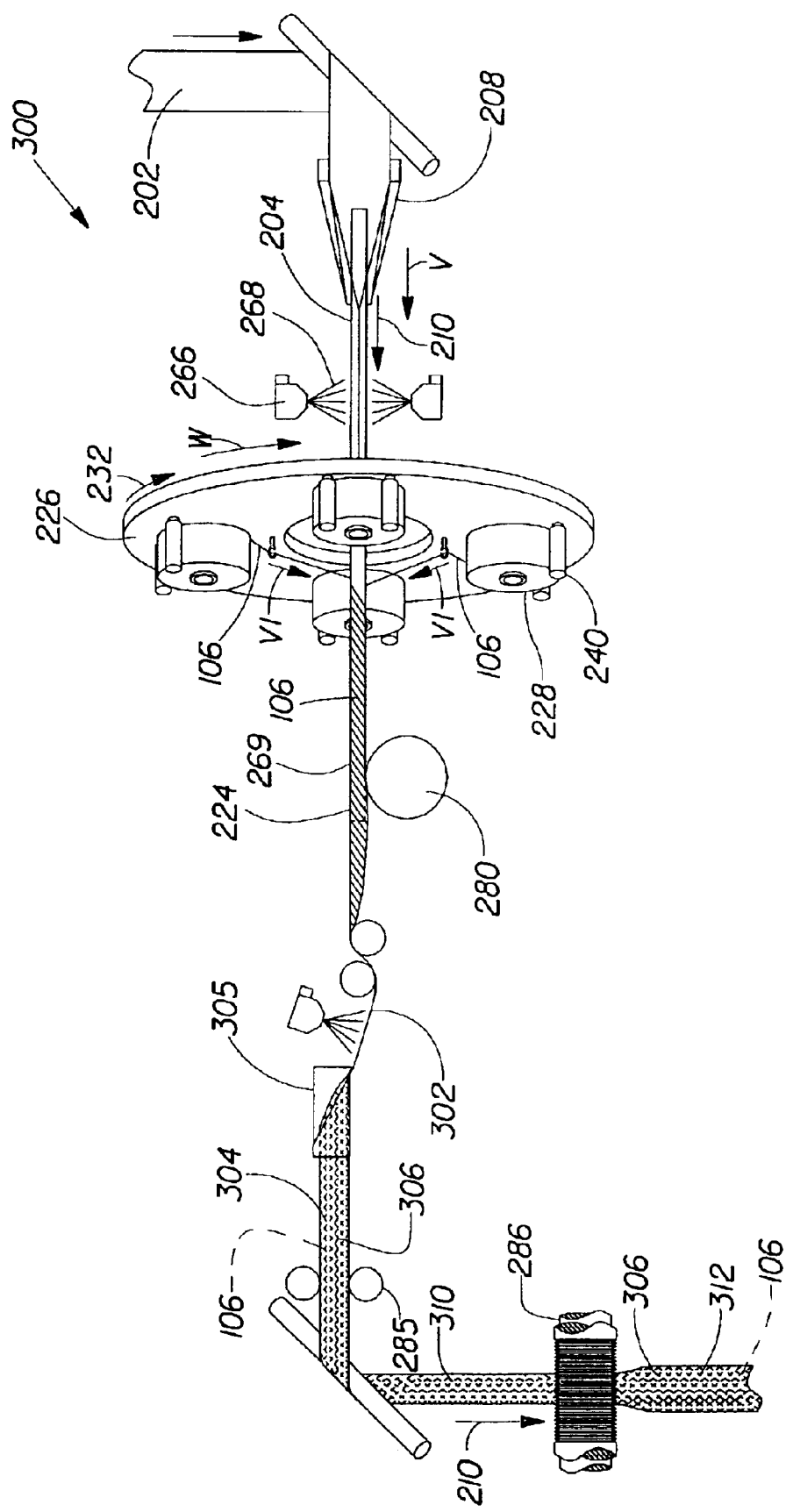
FIG. 7 is a simplified isometric view of another embodiment of the method and apparatus of the present invention.

FIG. 7 illustrates a simplified isometric view of another embodiment 300 of the method and apparatus of the present invention for producing an elasticized composite material 104A (see FIG. 2) of the present invention, having a crisscross configuration of elastic strips 106. In the embodiment 300 of FIG. 7, the first composite tube 269 can be produced similarly in all or any aspects to the embodiment 200 described herein above.

After the first composite tube 269 is produced, it can be then slit longitudinally by the slitting device 280 (described herein above) so as to open the slit first composite tube 269 longitudinally to form a first planar composite material 302 by any suitable unfolding device (not shown). The first planar composite material 302 can then be folded longitudinally into any suitable number of folds (for example, a bi-fold configuration 303 is shown in FIG. 7) by any suitable folding device 305 known to one skilled in the art so as to form a second planar composite material 304 having the elastic strips 106 disposed inside of the second planar composite material 302 and forming a crisscross pattern 306.

The second planar composite material 304 can be a latent elastic material 310 comprising elastic strips 106 in a crisscross pattern 306 in a substantially relaxed or stretched condition bonded between two folded parts of the first substrate 202. If the substrate 202 is not elastic, then the latent elastic material 310 is not elastic. The latent elastic material 310 can then be elasticized by the activation device 286, described above, to produce an elasticized composite material 312 having elastic strips 106 forming a crisscross pattern 306.

Figure 8:
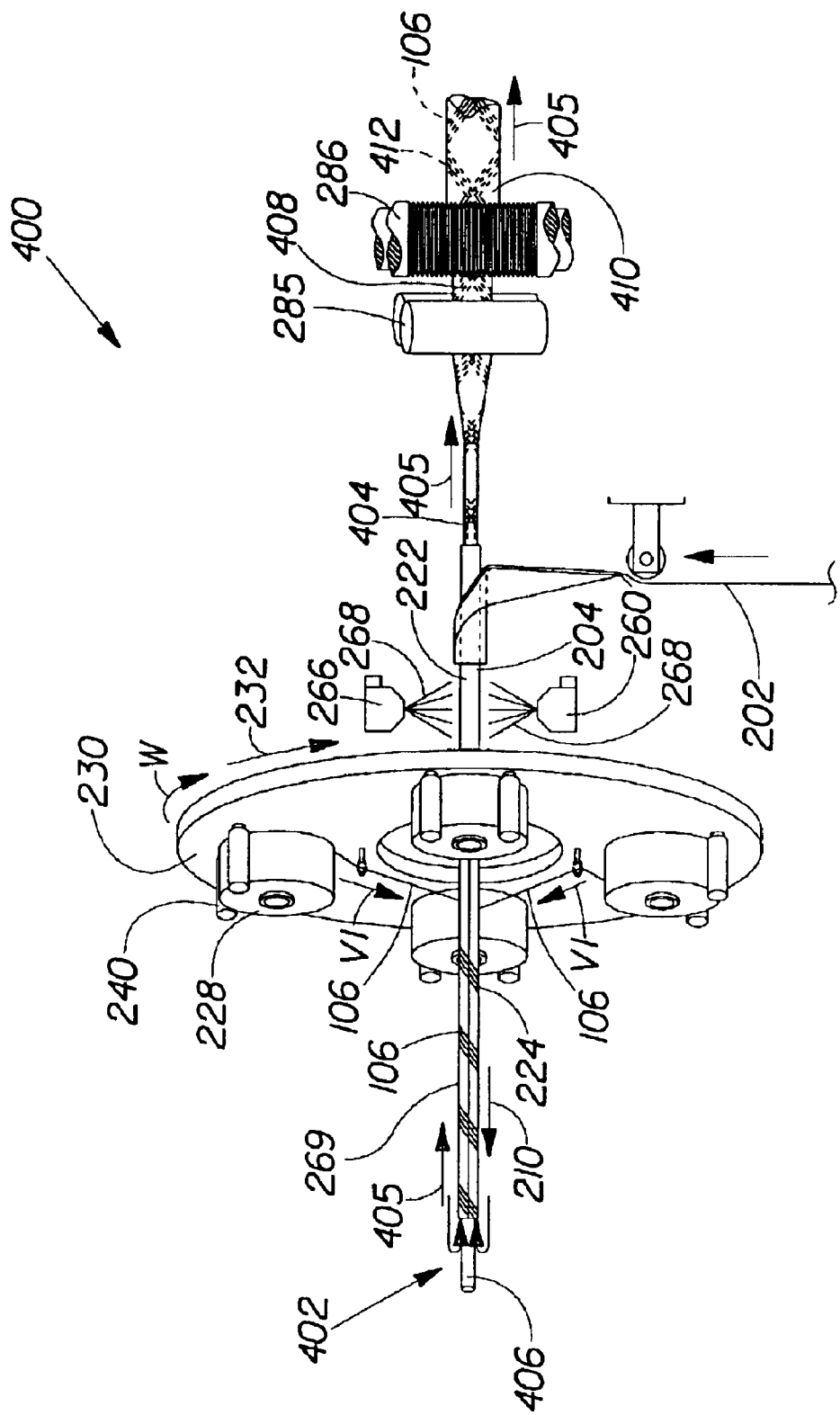
FIG. 8 is a simplified isometric view of another embodiment of the method and apparatus of the present invention.

FIG. 8 illustrates a simplified isometric view of another embodiment 400 of the method and apparatus of the present invention for producing an elasticized composite material 104A of the present invention by use of an inverse folding device 402 for inverting the first composite tube 269. Prior to the inverse folding device 402, the first composite tube 269 (having elastic strips 106 wound onto the outer surface 222 of the tube 204, i.e., facing outside of the tube), can be produced similarly to the embodiments 200 and/or 300 described herein above. The inverse folding device 402 call be any suitable folding device known to one skilled in the art capable to inverse-fold the first composite tube 269 into an inverted tube 404 having the outer surface 222 with elastic strips 106 turned inside of the invert tube 404. The inverse folding device 402 can optionally include any suitable assisting device 406 disposed inside the inverted tube 404 to assist the formation and the movement of the inverted tube 404 along an inversed direction 405 that is opposite to the direction 210. For example, the assisting device 406 can be a solid or a tube, can be heated or chilled, can include pressurized gas, can be stationary or moving.

The inverted tube 404 can then be flattened by any suitable nip device 285 to produce a latent composite material 408, which then can be activated by the activation device 286 to produce an elasticized composite material 410 having a crisscross configuration 412 of elastic strips 106.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A method of manufacturing an elasticized composite material including one or more elastic strips, the method comprising the steps of:
    (a) providing a mandrel;
    (b) providing a tube;
    (c) feeding the tube onto the mandrel such that the mandrel extends longitudinally inside the tube;
    (d) providing at least one elastic strip;
    (e) moving the tube longitudinally at a first velocity and simultaneously winding the at least one elastic strip around an outer surface of the tube at a second velocity to form a helical path;
    (f) joining the at least one elastic strip to the outer surface of the tube at least partially along the helical path to form a first composite tube;
    (g) folding a second substrate around the first composite tube to cover the at least one elastic strip to form a second composite tube;
    (h) slitting the second composite tube longitudinally to open the second composite tube;
    (i) unfolding the slit second composite tube to form a planar composite material; and
    (j) activating the planar composite material to form the elasticized composite material.

2. The method of claim 1, wherein the mandrel is stationary.

3. The method of claim 1, wherein the mandrel has a cross-section shape selected from the group consisting of a circle, an oval, a triangle, a square, a trapezoid, a parallelogram, a polygon, and any combination thereof.

4. The method of claim 1, wherein the tube is formed by a method comprising the step of folding a first substrate via a folding device.

5. The method of claim 1, wherein the first substrate is selected from a group consisting of a woven fabric, a knit fabric, a nonwoven fabric, a polymeric film, an elastic film, an elastic breathable film or any combination thereof.

6. The method of claim 1, wherein the first velocity or the second velocity varies.

7. The method of claim 1, wherein the at least one elastic strip is selected from a group consisting of a natural rubber, a synthetic rubber, polyurethane elastomers, polyisoprene elastomers, styrene-isoprene-styrene elastomers, block copolymer elastomers and any combination thereof.

8. The method of claim 1, wherein the at least one elastic strip has a cross-sectional shape selected from a group consisting of a rectangle, a trapezoid, a round, an oval and any combination thereof.

9. A method of manufacturing an elasticized composite material including one or more elastic strips, the method comprising the steps of:
    (a) providing a first substrate;
    (b) providing a mandrel;
    (c) folding the first substrate around the mandrel to form a tube;
    (d) providing at least one elastic strip;
    (e) moving the tube longitudinally at a first velocity and simultaneously winding the at least one elastic strip around an outer surface of the tube at a second velocity to form a helical path;
    (f) joining the at least one elastic strip to the outer surface of the tube at least partially along the helical path to form a first composite tube;
    (g) folding a second substrate around the first composite tube to cover the at least one elastic strip to form a second composite tube;
    (h) slitting the second composite tube longitudinally to open the second composite tube;
    (i) unfolding the slit second composite tube to form a planar composite material; and
    (j) activating the planar composite material to form the elasticized composite material.

10. The method of claim 9, wherein the mandrel is stationary.

11. The method of claim 9, wherein the mandrel has a cross-section shape selected from the group consisting of a circle, an oval, a triangle, a square, a trapezoid, a parallelogram, a polygon, and any combination thereof.

12. The method of claim 9, wherein the first substrate is selected from a group consisting of a woven fabric, a knit fabric, a nonwoven fabric, a polymeric film, an elastic film, an elastic breathable film or any combination thereof.

13. The method of claim 9, wherein the first velocity or the second velocity varies.

14. The method of claim 9, wherein the at least one elastic strip is selected from a group consisting of a natural rubber, a synthetic rubber, polyurethane elastomers, polyisoprene elastomers, styrene-isoprene-styrene elastomers, block copolymer elastomers and any combination thereof.

15. The method of claim 9, wherein the at least one elastic strip has a cross-sectional shape selected from a group consisting of a rectangle, a trapezoid, a round, an oval and any combination thereof.

16. A method of manufacturing an elasticized composite material including one or more elastic strips, the method comprising the steps of:
   (a) providing a substrate;
   (b) providing a mandrel;
   (c) folding the substrate around the mandrel to form a tube;
   (d) providing at least one elastic strip;
   (e) moving the tube longitudinally at a first velocity and simultaneously winding the at least one elastic strip around an outer surface of the tube at a second velocity to form a helical path;
   (f) joining the at least one elastic strip to the outer surface of the tube at least partially along the helical path to form a composite tube;
   (g) slitting the composite tube longitudinally to open the composite tube;
   (h) unfolding the slit composite tube to form a first planar composite material;
   (i) folding the first planar composite material longitudinally forming a second planar composite material having the elastics strips disposed inside of the second planar composite material forming a crisscross pattern; and
   (j) activating the second planar composite material to form the elasticized composite material.

17. The method of claim 16, wherein the mandrel is stationary.

18. The method of claim 16, wherein the mandrel has a cross-section shape selected from the group consisting of a circle, an oval, a triangle, a square, a trapezoid, a parallelogram, a polygon, and any combination thereof.

19. The method of claim 16, wherein the first substrate is selected from a group consisting of a woven fabric, a knit fabric, a nonwoven fabric, a polymeric film, an elastic film, an elastic breathable film or any combination thereof.

20. The method of claim 16, wherein the first velocity or the second velocity varies.

21. The method of claim 16, wherein the at least one elastic strip is selected from a group consisting of a natural rubber, a synthetic rubber, polyurethane elastomers, polyisoprene elastomers, styrene-isoprene-styrene elastomers, block copolymer elastomers and any combination thereof.

22. The method of claim 16, wherein the at least one elastic strip has a cross-sectional shape selected from a group consisting of a rectangle, a trapezoid, a round, an oval and any combination thereof.

23. A method of manufacturing an elasticized composite material including one or more elastic strips, the method comprising the steps of:
   (a) providing a substrate;
   (b) providing a mandrel;
   (c) folding the substrate around the mandrel to form a tube;
   (d) providing at least one elastic strip;
   (e) moving the tube longitudinally at a first velocity and simultaneously winding the at least one elastic strip around an outer surface of the tube at a second velocity to form a helical path;
   (f) joining the at least one elastic strip to the outer surface of the tube at least partially along the helical path to form a composite tube;
   (g) inverse-folding the composite tube to form an inverted tube having the outer surface of the tube turned inside of the tube; and
   (h) activating the inverted tube to form the elasticized composite material.

* * * * *

UNITED STATES PATENT AND TRADEMARK OFFICE
CERTIFICATE OF CORRECTION

PATENT NO.   : 6,855,223 B2
DATED        : February 15, 2005
INVENTOR(S)  : Johnson It is certified that error appears in the above-identified patent and that said Letters Patent is hereby corrected as shown below:

Column 8,
Line 43, delete "Bell" and insert -- Buell --.

Column 9,
Line 33, delete "call" and insert -- can --.

Signed and Sealed this

Fourth Day of October , 2005

JON W. DUDAS
*Director of the United States Patent and Trademark Office*

UNITED STATES PATENT AND TRADEMARK OFFICE
CERTIFICATE OF CORRECTION

PATENT NO.     : 6,855,223 B2
DATED          : February 15, 2005
INVENTOR(S)    : Johnson It is certified that error appears in the above-identified patent and that said Letters Patent is hereby corrected as shown below:

<u>Column 8,</u>
Line 43, delete "Bell" and insert -- Buell --.

<u>Column 9,</u>
Line 33, delete "call" and insert -- can --.

Signed and Sealed this

Eleventh Day of October, 2005

JON W. DUDAS
*Director of the United States Patent and Trademark Office*